US00PP32749P2

(12) United States Plant Patent
Klemm et al.

(10) Patent No.: US PP32,749 P2
(45) Date of Patent: Jan. 12, 2021

(54) ***DIANTHUS* PLANT NAMED 'KLEDP19289'**

(50) Latin Name: *Dianthus caryophyllus*
Varietal Denomination: KLEDP19289

(71) Applicant: Klemm+Sohn GmbH & Co. KG, Stuttgart (DE)

(72) Inventors: Nils Klemm, Stuttgart (DE); Lena Thiede, Bempflingen (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/873,272

(22) Filed: Mar. 10, 2020

Related U.S. Application Data

(60) Provisional application No. 62/973,971, filed on Nov. 4, 2019.

(51) Int. Cl.
*A01H 5/02* (2018.01)
*A01H 6/30* (2018.01)

(52) U.S. Cl.
USPC ..... Plt./273
CPC ..... *A01H 6/305* (2018.05)

(58) Field of Classification Search
USPC ..... Plt./273
CPC ..... A01H 6/305; A01H 5/02
See application file for complete search history.

*Primary Examiner* — Keith O. Robinson
(74) *Attorney, Agent, or Firm* — Weatherly IP Solutions, LLC; Barbara Campbell

(57) ABSTRACT

A new *Dianthus* plant designated 'KLEDP19289' particularly distinguished by salmon-pink double flowers, composed in round, small sprays and an upright habit, is disclosed.

1 Drawing Sheet

Genus and species: *Dianthus caryophyllus*.
Variety denominations: 'KLEDP19289'.

BACKGROUND OF THE NEW PLANT

The present invention comprises a new and distinct variety of *Dianthus*, botanically known as *Dianthus caryophyllus*, and hereinafter referred to by the variety name 'KLEDP19289'. 'KLEDP19289' originated from a cross from between the female *Dianthus* parent 'DCP-2009-0047' (unpatented) and the male *Dianthus* parent 'DCP-2007-0035' (unpatented) in The Netherlands in summer 2014.

In September 2015, 'KLEDP19289' was first vegetatively propagated by vegetative stem cuttings. 'KLEDP19289' was found to reproduce true to type in successive generations of asexual propagation in Stuttgart, Germany via vegetative stem cuttings.

SUMMARY

The following are the most outstanding and distinguishing characteristics of 'KLEDP19289' when grown under normal horticultural practices in Latina, Italy and Stuttgart, Germany.

1. Salmon-pink double flowers, composed in round, small sprays; and
2. An upright habit.

DESCRIPTION OF THE PHOTOGRAPH

This new *Dianthus* plant is illustrated by the accompanying photograph. The photograph shows the whole plant, including the flowers and foliage and buds. The colors shown are as true as can be reasonably obtained by conventional photographic procedures. The photo is of an 11-week-old plant of 'KLEDP19289'. The photo was taken in Stuttgart, Germany indoors, in April 2016.

DESCRIPTION OF THE NEW VARIETY

The following detailed descriptions set forth the distinctive characteristics of 'KLEDP19289'. The data which define these characteristics were collected from asexual reproductions carried out in Latina, Italy. Data was collected in May 2019 on plants that were potted in week 38 of 2018. Color references are to The R.H.S. Colour Chart of The Royal Horticultural Society of London (R.H.S.), 5$^{th}$ edition (2007).

Classification:
- *Family*.—Caryophyllaceae.
- *Botanical*.—*Dianthus caryophyllus*.
- *Common*.—Pot carnation.
- *Designation*.—'KLEDP19289'.

Parentage:
- *Female parent*.—'DCP-2009-0047' (unpatented).
- *Male parent*.—'DCP-2007-0035' (unpatented).

Plant:
- *Propagation type*.—Vegetative stem cuttings.
- *Time to produce a rooted young plant*.—4 weeks.
- *Root description*.—Fine and white, RHS 161D, habit is lanceolate-shaped.
- *Plant form*.—Upright.
- *Plant height*.—23.0 cm.
- *Plant diameter or spread*.—26.0 cm.

Lateral branches:
- *Length*.—22.0 cm.
- *Diameter*.—0.2 cm.
- *Internode length*.—5.0 cm.
- *Node length*.—0.4 cm.
- *Node diameter*.—0.1 cm.

*Texture*.—Smooth.
*Color*.—RHS 137B (Green).
*Flower clustering on the lateral branch*.—In some lateral branches.
*Number of internodes*.—6.
*Shape of stem in cross-section*.—Circular.
*Hollowness of the stem*.—Absent.

Foliage:
*Arrangement*.—Opposite.
*Length*.—5.0 cm.
*Width*.—0.6 cm.
*Shape*.—Lanceolate.
*Apex*.—Acute.
*Base*.—Obtuse.
*Margin*.—Entire.
*Texture* (*both upper and lower surfaces*).—Smooth.
*Cross section of the leaf*.—Moderately concave.
*Curvature of the leaf*.—Absent.
*Glaucosity of the leaf*.—Weak.
*Immature leaf color*.—Upper surface: RHS N137A (Green). Lower surface: RHS 137A (Green).
*Mature leaf color*.—Upper surface: RHS N137C (Green). Lower surface: RHS 137B (Green).
*Venation pattern*.—Parallel.
*Venation color* (*both upper and lower surfaces*).—RHS 137C (Green).

Flowers:
*Flower type and habit*.—Round, double, small sprays.
*Fragrance*.—Present, sweet.
*Natural flowering season*.—Spring to fall.
*Flower longevity on the plant*.—10 to 12 days.
*Position of flowers compared to the foliage of the plant*.—Moderately above.
*Profile of both the upper and lower part in the lateral view*.—Flat convex.
*Diameter of the flower*.—4.2 cm.
*Buds*.—Length: 1.6 cm. Diameter: 0.7 cm. Shape: Elliptic. Color: RHS 138A (Green). Extrusion of the styles of the bud: Absent.
*Corolla*.—Quantity of petals per flower: 34. Corolla height: 2.5 cm. Petal length: 3.8 cm. Petal width: 1.9 cm. Petal shape: Spoon-shaped. Petal apex: Obtuse. Petal base: Acute. Petal margin: Crenate. Petal texture (both upper and lower surfaces): Smooth. Petal color (both immature and mature): Upper surface: RHS 52C (Red). Lower surface: RHS 69A (Red-Purple). Macule: Absent.
*Calyx*.—Quantity of sepals per flower: Composed of 5 sepals. Shape: Cylindrical. Longitudinal axis of the lobes of the calyx: Straight. Calyx height: 2.2 cm. Calyx diameter (at the apex): 0.6 cm. Sepal texture (both upper and lower surfaces): Smooth. Sepal color: Upper surface: RHS 137B (Green). Lower surface: RHS 144C (Yellow-Green).

Peduncles:
*Length*.—1.5 cm.
*Diameter*.—0.1 cm.
*Strength*.—Medium strong.
*Texture*.—Smooth.
*Color*.—RHS 137B (Green).

Reproductive organs:
*Stamens*.—Quantity per flower: 8. Filament length: 2.3 cm. Filament color: RHS 155B (White). Anther length: 0.2 cm. Anther diameter: 0.1 cm. Anther color: RHS 158A (Yellow-White). Pollen amount: None observed.
*Pistils*.—Quantity per flower: 1. Pistil length: 2.5 cm. Style length: 1.7 cm. Style shoulder: Absent. Number of styles per flower: 2. Style color: RHS NN155A (White). Stigma shape: Filamentous. Stigma color: RHS 70C (Red-Purple). Ovary size: 0.7 cm. Ovary shape: Oval. Ovary color: RHS 145A (Yellow-Green). Ovary surface texture: Smooth.

Fruit and seed set: None observed.

Disease and pest/insect resistance: No disease and pest/insect resistance observed.

COMPARISON OF 'KLEDP19289' WITH PARENTAL LINES AND KNOWN VARIETY

'KLEDP19289' is distinguished from the parental lines as described in Table 1.

TABLE 1

Comparison with Parental Lines

| Characteristic | 'KLEDP19289' | Female Parent 'DCP-2009-0047' | Male Parent 'DCP-2007-0035' |
|---|---|---|---|
| Flower color | Salmon-pink | Yellow with purple stripes | Light pink |

'KLEDP19289' can be compared to the commercial *Dianthus* variety 'Sorbet' (unpatented). Differences between the varieties are described in Table 2.

TABLE 2

Comparison with Similar Variety

| Characteristic | 'KLEDP19289' | 'Sorbet' |
|---|---|---|
| Flower color | Salmon-pink | Yellow-orange |
| Earliness to flower | Early | Medium-early |

We claim:

1. A new and distinct variety of *Dianthus* plant designated 'KLEDP19289' as illustrated and described herein.

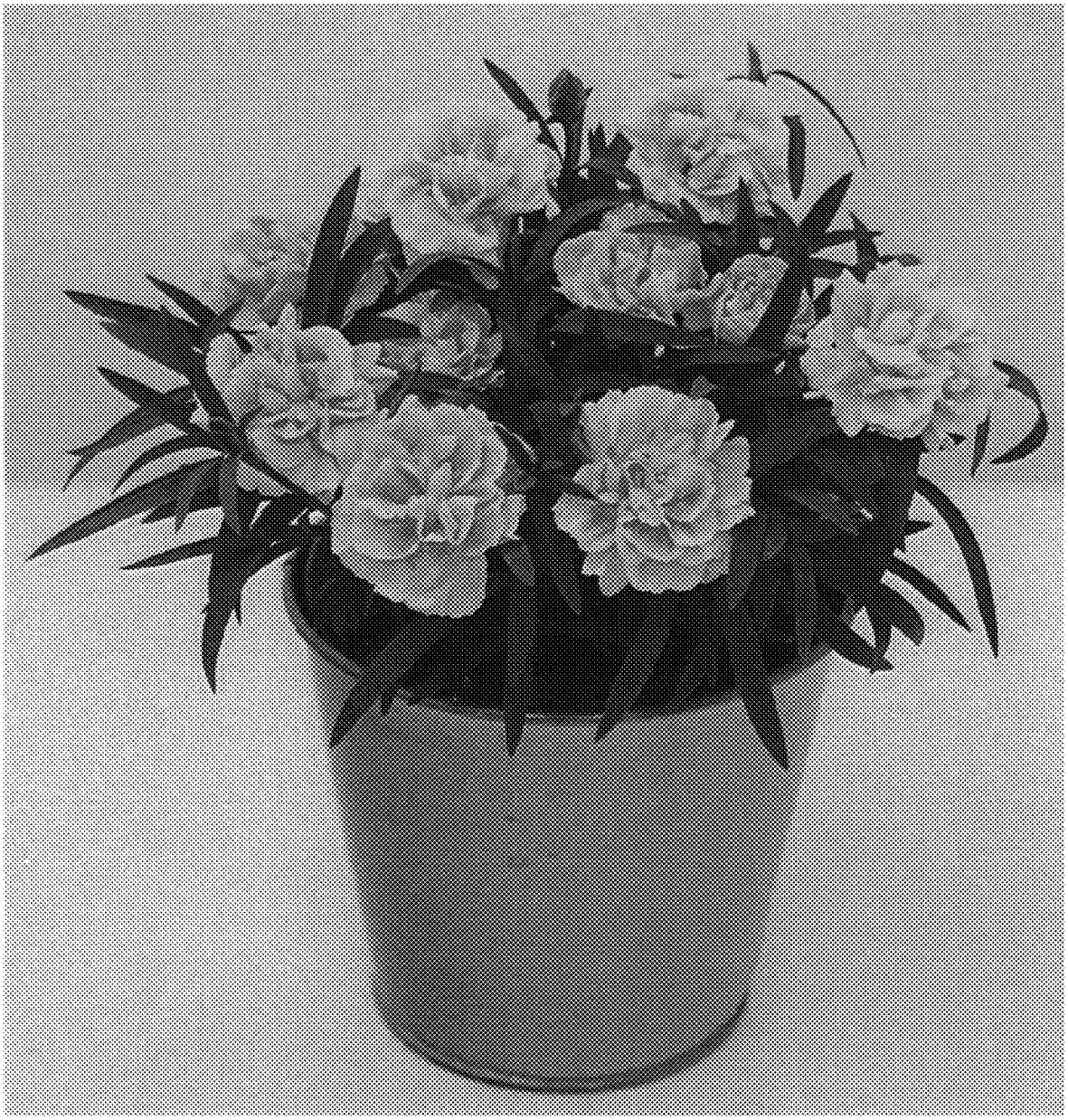

* * * * *